United States Patent [19]
Balamuth et al.

[11] 3,941,424
[45] Mar. 2, 1976

[54] ULTRASONIC TOOTHBRUSH APPLICATOR

[75] Inventors: Lewis Balamuth, Southampton; Michael R. Rutten, East Islip; Robert Meyer, Huntingdon Station, all of N.Y.

[73] Assignee: Ultrasonic Systems, Inc., Farmingdale, N.Y.

[22] Filed: June 7, 1974

[21] Appl. No.: 477,306

Related U.S. Application Data

[62] Division of Ser. No. 318,430, Dec. 26, 1972, Pat. No. 3,840,932.

[52] U.S. Cl. ................................................. 300/21
[51] Int. Cl.² ........................................... A46D 3/04
[58] Field of Search ....................................... 300/21

[56] References Cited
UNITED STATES PATENTS

| | | | |
|---|---|---|---|
| 1,238,635 | 8/1917 | Chandler et al. | 300/21 |
| 2,390,437 | 12/1945 | Hayes | 300/21 |
| 2,558,334 | 6/1951 | Baumgartner | 300/21 X |
| 2,587,792 | 3/1952 | Von Sivers | 300/21 X |
| 2,878,069 | 3/1959 | Wessel, Jr. | 300/21 |
| 3,086,820 | 4/1963 | Baumgartner | 300/21 |

Primary Examiner—Granville Y. Custer, Jr.

[57] ABSTRACT

This invention relates to the method of manufacturing a toothbrush adapted to be mounted on an automatic toothbrush power handle, and having as a power source vibratory energy in the ultrasonic range. The manufacturing process includes that of providing a plastic brush having a head portion including a plurality of apertures and positioning a bristle cluster respectively in each aperture; and effecting a flow of the plastic in the head portion into substantially surrounding relationship of the bristles in each aperture therein, such that the plastic solidifies in adhesive relationship to the bristles to transmit the ultrasonic vibratory energy from the brush head portion to the bristles.

25 Claims, 28 Drawing Figures

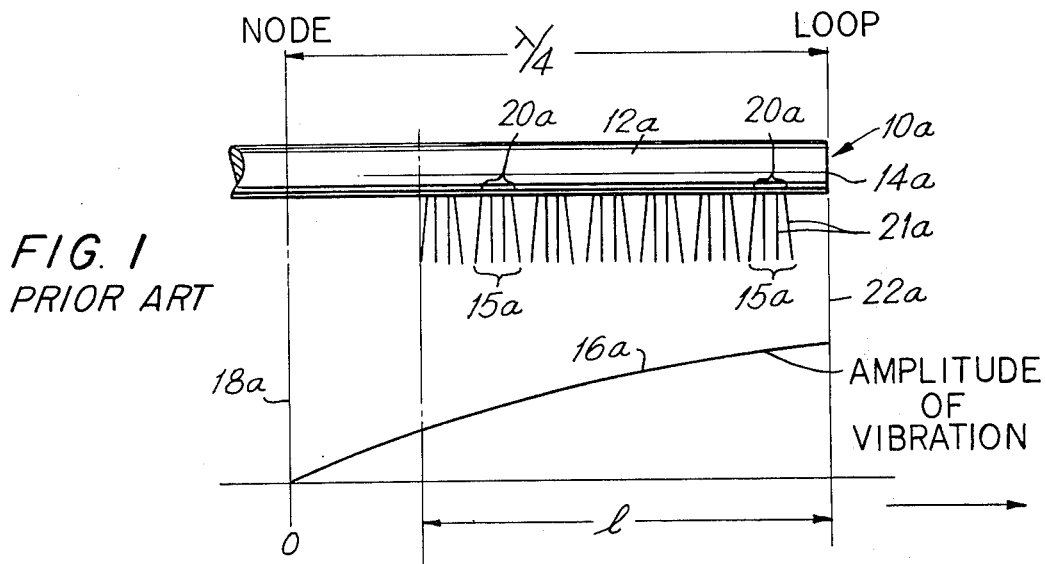
FIG. 1 PRIOR ART
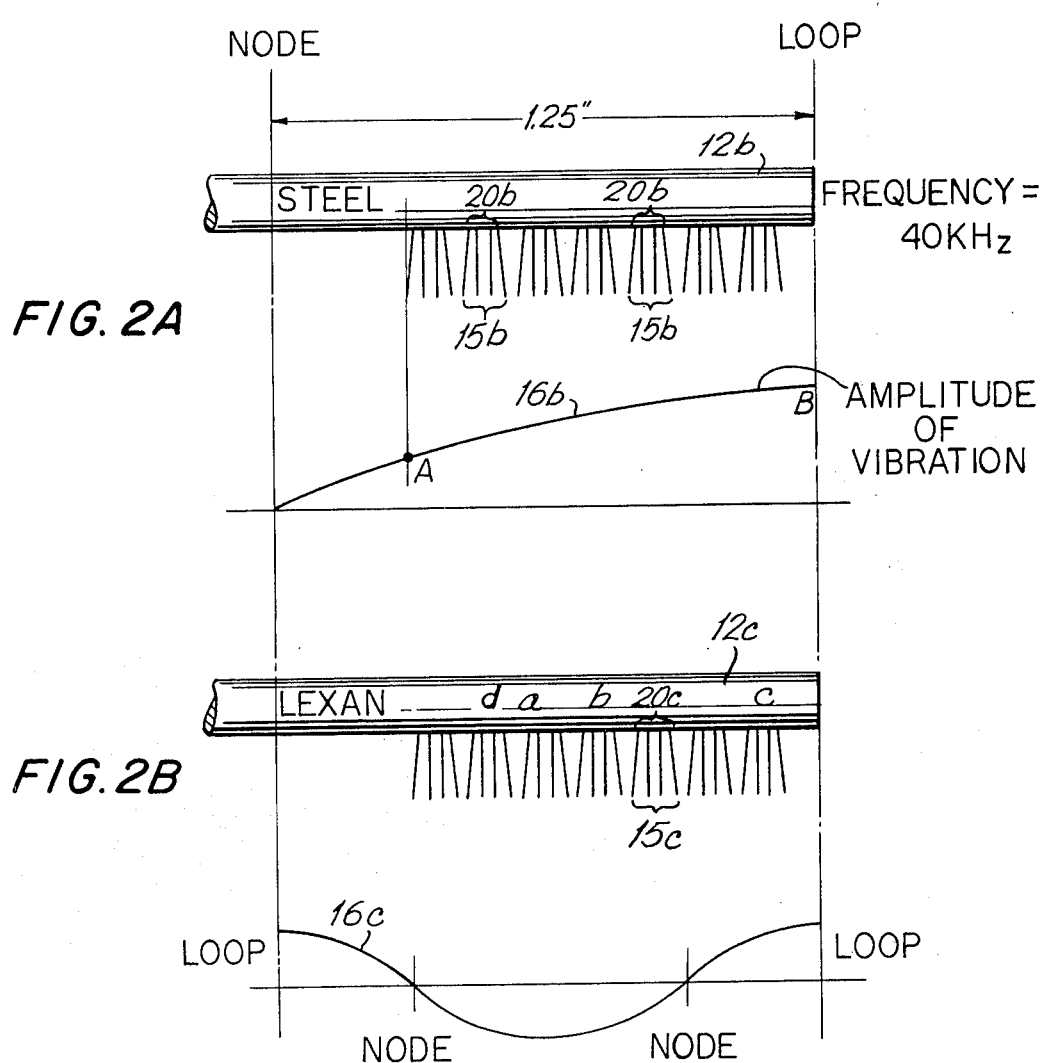
FIG. 2A
FIG. 2B $\lambda$ = WAVE LENGTH (LONGITUDINAL VIBRATION) IN EACH SECTION OF THE LINE SHOWN

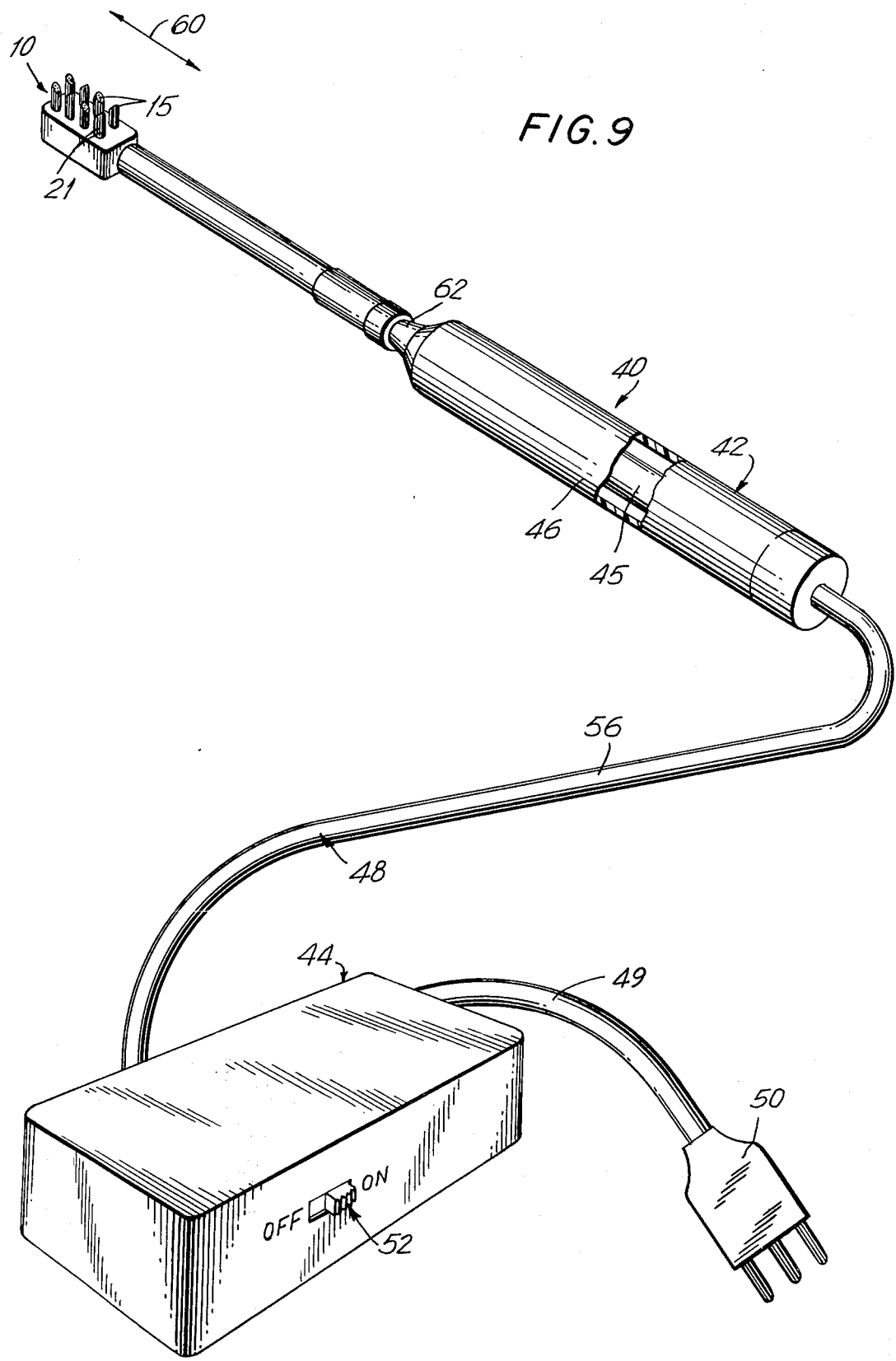

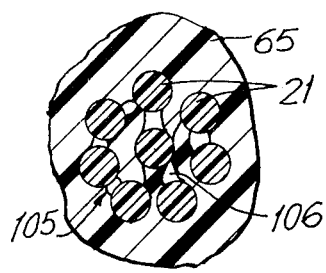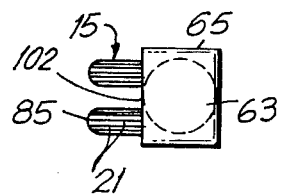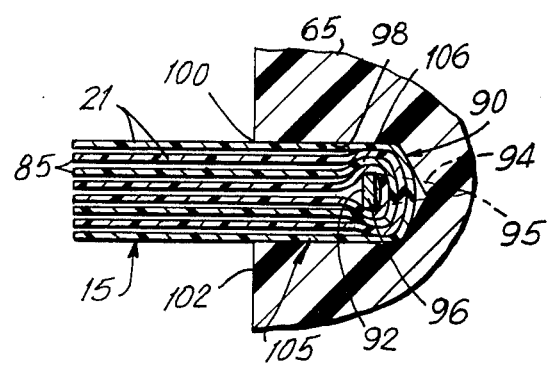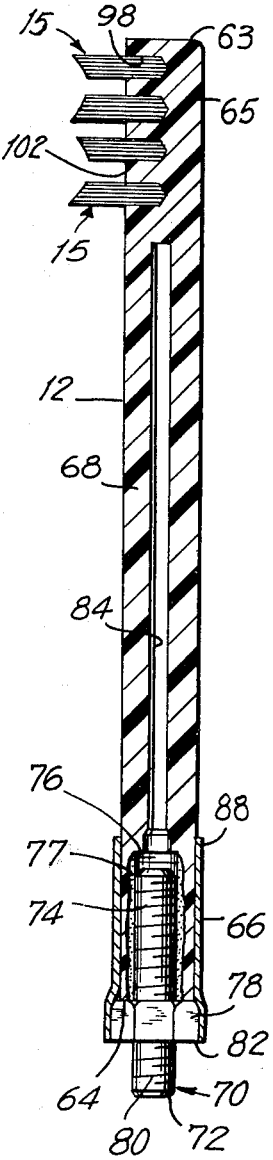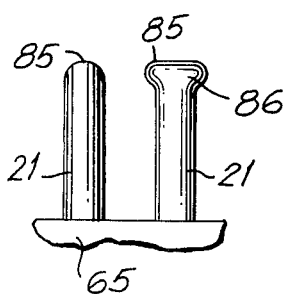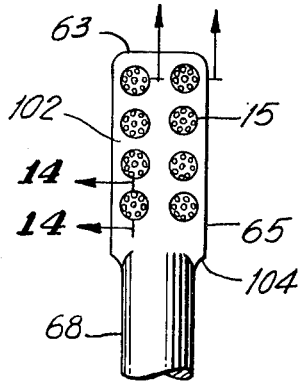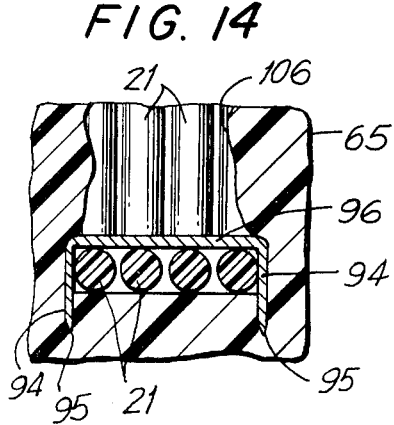

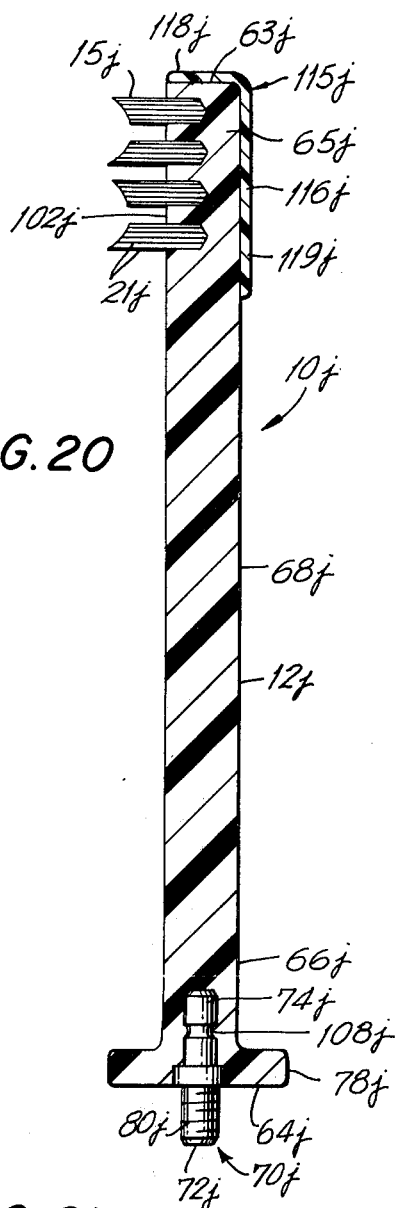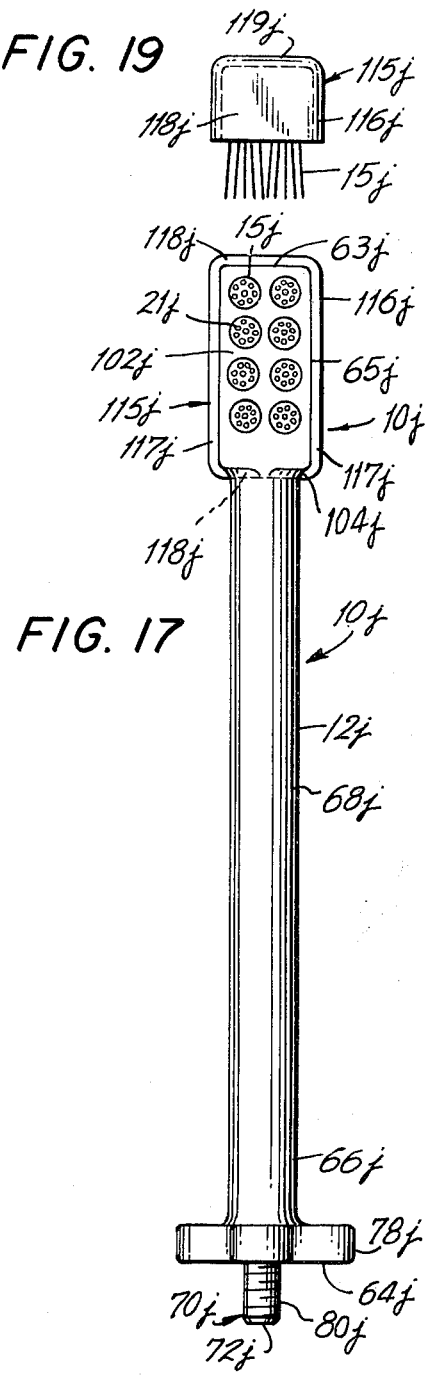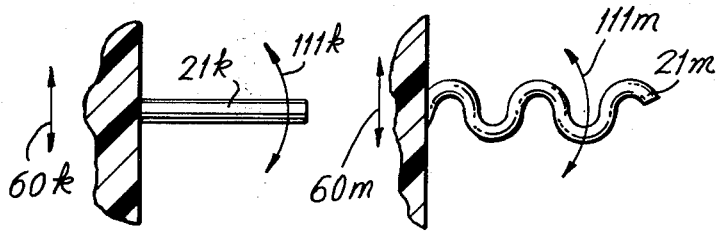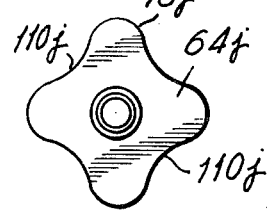

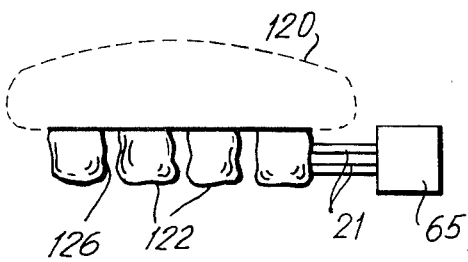
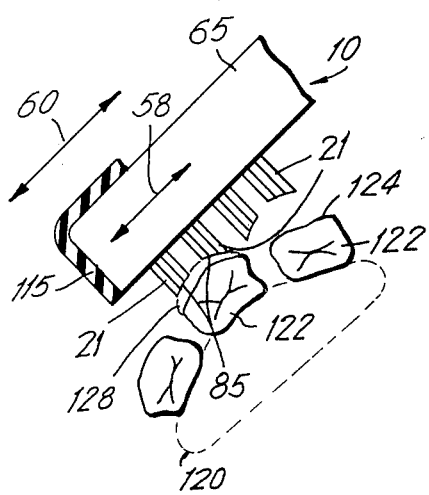
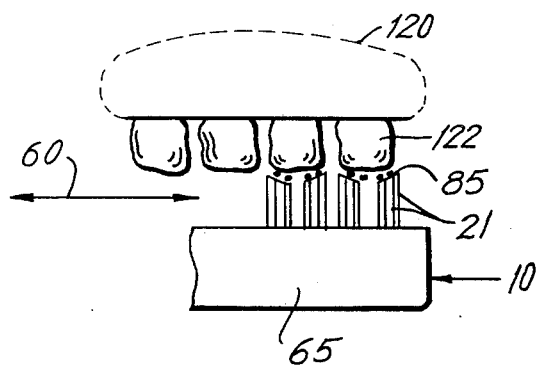
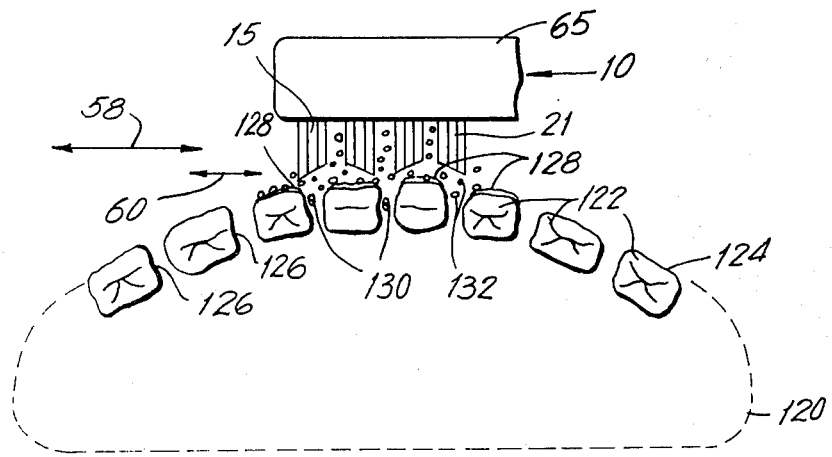

ULTRASONIC TOOTHBRUSH APPLICATOR

CROSS-REFERENCE TO RELATED APPLICATIONS

This is a division of application Ser. No. 318,430 filed Dec. 26, 1972 now U.S. Pat. No. 3,840,932 issued Oct. 15, 1974.

In a co-pending patent application of Lewis Balamuth, Arthur Kuris, and Manual Karatjas, Ser. No. 318,428, filed Dec. 26, 1972, now U.S. Pat. No. 3,828,770 issued Aug. 13, 1974, for Ultrasonic Method For Cleaning Teeth and assigned to the assignee of the present invention, an ultrasonic system that may be used as for oral cleaning is shown having a brush applicator that may be designed in accordance with the present invention.

BACKGROUND OF THE INVENTION

This invention relates to the dental field and more particularly to a toothbrush designed for and compatible with an automatic toothbrushing system which is powered in the sonic and ultrasonic range for inducing vibrations therein.

The applicants have found that for commercial application of their invention it would be desirable for home use to utilize a brush head made substantially of plastic and not of a metallic material as disclosed in U.S. Pat. No. 3,335,443. In order to achieve the assembly of brushes having a plastic body on a mass production basis, they required certain novel procedures and designs in order to obtain these results.

OBJECTS OF THE INVENTION

One object of the invention is to provide a novel applicator to be used in the ultrasonic energy range.

Accordingly, another object of this invention is to provide a toothbrush especially designed for use with a sonic-ultrasonic powered system in order that improved cleaning and polishing may be achieved at the same time gingival health benefits are obtained.

Another object of the invention is to provide a toothbrush head designed for compatible use from an ultrasonic power source.

Another object of the present invention is the provision of a brush head in which plastic tip bristles and plastic head brushes are coupled together for the transmission of ultrasonic and sonic energy for the individual bristle elements.

Other objects of the invention will become apparent as the disclosure proceeds.

SUMMARY OF THE INVENTION

The present invention provides for an interchangeable toothbrush assembly that when coupled to an ultrasonic motor is adapted to be vibrated at an ultrasonic rate and simultaneously therewith at a sonic rate while the motor may be hand held and the bristle clusters of the brush are utilized for the removal of foreign deposits from teeth. In order to assure the proper transmission of high frequency energy from the body portion of the brush to the individual bristles, appropriate securing means are employed such that the relation of the plastic bristles to the plastic body portion are properly matched and energy is transmitted.

As hereinafter discussed, there is a defined relationship between the spacing of the bristle clusters and the selection of the material from which the body portion of the brush is fabricated so as to assure a proper vibratory energy transmission. The applicator means or brushes of the present invention may have individual bristle diameters and a resistance factor to obtain maximum cleaning efficiency. For example, it has been found that a brush having bristle clusters that range in the diameter of 0.004 inch to 0.020 inch and having approximately 80 bristles per cluster at 0.008 diameter generally form a bristle configuration to which the energy may be properly transmitted and yet also properly clean.

Another aspect of the invention resides in the fact that the output end of the bristle clusters may be contoured so as to accept the configuration of the teeth as same is positioned within the oral cavity for use by the user such that the brush may be placed, if desired, in relatively fixed position against the teeth so as to maintain it in a relatively fixed position as the energy from the bristle tufts is transmitted to obtain the cleaning results.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a diagrammatic view of applicator means in accordance with the prior art to help illustrate the theory of the present invention;

FIG. 2A is a diagrammatic view, similar to FIG. 1, of applicator means having a metallic body and vibrated at a particular frequency of vibration, to help illustrate the theory of the present invention;

FIG. 2B is a diagrammatic view, similar to FIG. 2, of applicator means having a Lexan body and a representation of the vibration pattern associated therewith, to help illustrate the theory of the present invention;

FIG. 9 is a perspective view of an ultrasonic home oral unit in accordance with the present invention;

FIG. 10 is an enlarged sectional view illustrating applicator means in accordance with the present invention;

FIG. 11 is an end view of the applicator means illustrated in FIG. 10;

FIG. 12 is a fragmentary elevational view of a portion of the applicator means in accordance with the present invention;

FIG. 13 is an enlarged fragmentary sectional view taken substantially along the line 13—13 in FIG. 12;

FIG. 14 is an enlarged fragmentary sectional view taken substantially along the line 14—14 in FIG. 12;

FIG. 15 is an enlarged fragmentary sectional view illustrating the individual bristles secured in position;

FIG. 16 is an enlarged fragmentary view illustrating the rounded bristle ends;

FIG. 17 is a front view of another form of applicator means in accordance with the present invention;

FIG. 18 is a bottom view of the applicator means in FIG. 17;

FIG. 19 is a top view of the applicator means in FIG. 17;

FIG. 20 is an enlarged side view in cross-section of the applicator means of FIG. 17;

FIGS. 21 and 22 are enlarged diagrammatic views of bristle elements;

FIG. 23 is a view which illustrates the applicator means of the present invention in relation to the gingiva and tooth structures of a human to obtain a cleansing action, and helpful in explaining the process of the present invention;

FIG. 24 is a view which illustrates the applicator means in position to the upper surface of the teeth in the oral cavity;

FIG. 25 is a view which illustrates the applicator means in positon to the front exposed surfaces of the teeth in the oral cavity;

FIG. 26 is a partial view illustrating the applicator means in positon to the surfaces of the teeth and illustrating the components of vibratory motion related thereto;

DETAILED DESCRIPTION OF THE DRAWINGS

Figure 3:
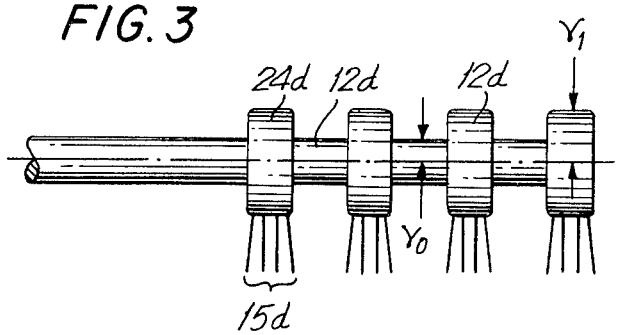
FIG. 3 is a diagrammatic view illustrating an embodiment of the invention in which the applicator means has spaced apart body sections with bristles extending radially therefrom.

The ultrasonic applicator means of the present invention, as hereinafter discussed with respect to FIGS. 1–6, is dependent upon an interrelated number of characteristics in order to function in a desired manner.

Prior art disclosure of ultrasonic toothbrush design requires that the ultrasonic activity of each bristle cluster pair diminishes proportionately to their position or distance from said bristle holding toothbrush section or element. Thus, it was desirable to make the applicator means operate at the lowest possible ultrasonic frequency so that the wave length of waves in the body section would be as long as possible, thereby diminishing the effect of displacement from the free end. It was recognized that this frequency limitation seriously hampered the freedom to design the most effective brush head for optimal cleaning and other effects inherent in the use of ultrasonic energy for the care of teeth and gingiva.

As FIG. 1 shows diagrammatically in accordance with the prior art for a toothbrush 10a having a body section 12a of a metallic material which forms the bristle cluster base which shows the greater ratio of the cluster base, 1, to the loop-node ($\tau/4$) distance, the more will the amplitude of vibration of the bristle cluster base 12a diminish from its free maximum vibration end 14a as illustrated by the curve 16a which represents the amplitude of vibration from the node at the vertical plane at 18a in at which there is no longitudinal vibration to a loop of longitudinal vibration where the amplitude of vibration is maximum as indicated at the vertical plane 22a.

Now, the physical demands of toothbrush dynamics require a number of bristle clusters 15a each having a bristle base 20a and elements 21a of finite size (each cluster might have a base diameter of about 3/32 inch). Furthermore, these demands mean that to achieve ordinary toothbrush capacity, one must provide a length of vibratory base material which is at least of the order of a half inch up to one inch in magnitude. Now applicants recognized that conventional electric toothbrushes operating in the 60 vibrations per second range do not encounter the above problem because the "wave length," so to speak, becomes relatively infinite or at least so large that all the bristle clusters bases move in phase with the same reciprocating stroke.

Now, in order to enjoy the unique advantages and easy adaptability of the ordinary tooth form, applicants have discovered a way of designing a toothbrush to satisfy these requirements. The essence of applicants' invention resides in the discovery that there are acoustically efficient plastic materials with extremely low speeds of sound (or what is the same thing, low speeds of longitudinal vibrations). For example, a polycarbonate such as Lexan, has a speed of longitudinal waves in a rod of about one fourth the value of the speed of such waves in steel or aluminum at the same high frequency (i.e., above 20 KHz). This results from the fact of the extremely low value of the Young's Modulus of this plastic. Applicants have further discovered that it is possible to "load" the plastic rod with a dispersion of powder or other types of dense filler whereby its density may materially increase without a corresponding increase in Young's Modulus. This still further lowers the speed of longitudinal waves in such an element.

As a result, an analysis is provided in FIGS. 2A in which a steel rod, or body section 12b is illustrated as vibrated, at 40 KHz and compare it with a Lexan rod in FIG. 2B or body section 12c at the same frequency. Steel has a wave length of about 5 inches at 40 KHz and therefore a $\tau/4$ of 1.25 inch.

The Lexan corresponding $\tau/4$ will be approximately one fourth of the value for steel $\frac{1}{4} \times 1.25$ inch $= 0.36$ inch.

FIGS. 2A and 2B shows the difference of vibration as indicated by curve 16b for steel in distribution at 40 KHz for a steel rod with bristles and a Lexan rod as indicated by curve 16c with bristles. As will be seen later, the presence of the bristle clusters modifies the curves 16a (same as 16b ) and 16c in opposite senses, whereby optimal distribution of ultrasonic power density in the bristle clusters is favored in the case of curve 16c and is worsened in the case of curve 16a. Clearly the steel rod body section 12b shows a significant reduction in amplitude of the bases 20b of the bristle clusters 15b in going from point B to point A over an approximately ¾ inch distance. The Lexan body section 12c on the other hand shows a distribution of nodes and loops of vibration as illustrated by curve 16c within the same approximately ¾ inch section at the same frequency. As a result, it is possible to distribute the bristle clusters so as to take advantage of such sites as $a, b, c$ and $d$ (see FIG. 2B). In fact, it is evident that by simple design it is possible to obtain an extended toothbrush complement of bristle clusters 15c so that the vibration amplitude (and hence the efficiency of action) of all clusters may be monitored at about the same level.

This is a novel concept to this art and enables one to produce efficient, inexpensive toothbrushes operating in the ultrasonic frequency range. In addition, new design possibilities arise in relation to the transmission line design, which did not exist before, because the distance between bristle clusters is of the same order as the $\tau/4$ of the transmission line. It is intended to take advantage of all such possibilities within the scope of this invention. For example, consider a structure such as FIG. 3, which accomplishes the results desired by the use of a body section $12d$ having enlarged radial sections $24d$ with bristle clusters $15d$ extending radially therefrom.

Figure 4:
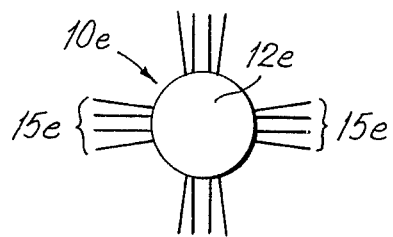
FIG. 4 is a diagrammatic view illustrating an embodiment of the invention in which the applicator means has bristle clusters that extend in radial arrays from the body section.

FIG. 4 illustrates the invention in which bristle clusters $15e$ may be in radial arrays from the body section $12e$ in such a manner that a multiple number of clusters exist in each plane of the brush $10e$.

Now, applicants have discovered, that in order to be able to produce a home oral device together with its necessary electronic converter, the most basic questions to be answered were those permitting increased efficiency of operation, adequate safety in home use in the mouth, and especially simplicity of design permitting low production costs for a mass-production product. One important part of this effort in the case of the applicator means or brush head was to guarantee good vibration energy transfer from the base to the bristle clusters without having recourse as in the prior art to relatively expensive epoxy bonding of such cluster in a metal base. Also, the effect shown in FIG. 3, and hereinafter discussed in greater detail, was to be made as simply as possible so as to achieve optimum spacing of bristle clusters relative to the standing wave pattern set up in the base during operation. This was done by a combination of factors whereby every element in the design entered into experimental work. For example, bristle diameters were selected which would produce a visible fog-like spray of water from the wet bristle head when vibrating in the motor-converter system of the invention. Also, a maximum number of bristles per cluster was used compatible with the cross-sectional dimensions of the base portion. In addition, specific advantage was taken in in inserting a bristle cluster by employing a well known mass production technique which caused a bristle cluster to be composed of a bundle of U-shaped plastic filaments, which are pushed into an aperture with the aid of a metal staple which stays with the bristle cluster after insertion. This mechanical technique is extremely fast and is preferably carried out with the thermoplastic base in a heated condition just below its creep temperature, so as to minimize static residual stresses due to the insertion. But, such mechanical insertion still leaves voids in the region of insertion which serve to lessen the transmitting efficiency of the bristles to the base insofar as vibration transmission is concerned. This difficulty was obviated by the simple expedient of dipping the brush head, after being formed, into a solution which acts as a better solvent for the thermoplastic base material than for the thermoplastic bristle material. For example, a preferred embodiment of the head would include Nylon bristles staple-mounted into a Lexan (polycarbonate plastic) base and blended with a solution of methylene chloride. The solvent can be applied either by a brief dip after mechanical fabrication or can be incorporated into the staple mounting operation by addition of a small amount of said solvent at that time.

In any case, the results achieved are typically hereinafter illustrated with respect to FIGS. 9–22, which shows the U-shaped bristle elements, in place with the cross-section of the metal staple showing. In addition, the spaces between the bristles are filled with the base material which has flowed into place due to the action of the added solvent, which is volatile and vanishes after performing its job. Thus a number of effects are simultaneously achieved whereby excellent acoustic or high frequency vibration coupling is achieved with minimal losses. For example, in practice, it has been found that, when an eight bristle cluster applicator head is mechanically coupled onto the motor output, a definitely visible spray from the bristles in a water wetted condition may be produced in the 30KHz range with input of only 2 watts into the motor. This recital of facts alone will illustrate to anyone skilled in the art that the instant type of brush head and body is extraordinarily efficient.

Figure 5:
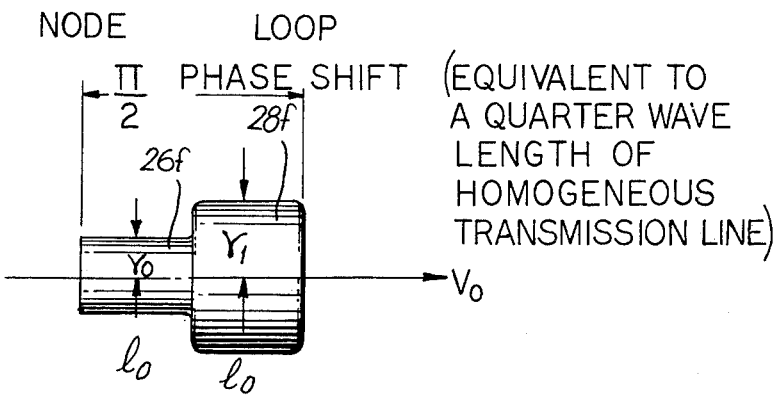
FIG. 5 is a diagrammatic view of a portion of applicator means in accordance with the present invention to illustrate the relation between frequency and the various dimensions of the applicator means.

In addition, the construction of FIG. 5 serves to bring about in part the condition shown in FIG. 3, without the alterations $r_0$ and $r_1$ of cross-section shown in FIG. 3. This is because the bristle clusters as shown, for example, at $b$ in FIG. 6 together with the metal staple, act as an increased mass in the section of the transmission line where it is inserted.

In order to understand this matter and its importance, we will consider in FIG. 5 a quarter wave transmission line for longitudinal or torsional vibrations as composed of two sections $26f$ and $28f$ of equal length. The line is shown as cylindrical for mathematical convenience, which in no way affects the force of the following argument. Now, the radii $r_0$ and $r_1$ and the length $l_0$, and the length $l_0$ are easily shown to be connected in the following equation $$\tan (2\ \pi l_0/\tau) = (r_0/r_1) = \alpha$$

In the case of a non-cylindrical line, then we may use the cross-sectional areas $A_0$ and $A_1$, and in this case $\alpha = A_0/A_1$, in the above equation. From the equation a simple table of values may be made as follows:

Table I

| $\alpha$ | $(2\ \pi l_0/\tau)$ Degrees |
|---|---|
| .32 | 17.8° |
| .45 | 24.3° |
| .63 | 32.3° |
| .77 | 37.6° |
| .89 | 41.6° |
| 1.00 | 45.0° |

As may be seen from the equation and the table, when $r_0$ is about one third of $r_1$, then the value of $2\pi l_0/\tau$ is 17.8° as compared with 45° when the two cross-sections are equal. This is equivalent to the conclusions that the $\pi/2$ phase shift shown in FIG. 5 takes place in a distance which is (17.8/45) = 0.4 of the distance required for uniform cross-section. Thus, in the previous example given in connection with FIG. 2, at 40 KHz, the value of $\tau/4$ was shown to be 0.36 inch in Lexan. With the alternating reduced cross sections of the FIG. 5 presentation, the equivalent $\tau/4$ or $\pi/2$ shift in phase would occur in a distance of 0.4 × 0.36 = .144 inch. The bristle clusters would still further reduce this phase shift distance. Thus, it is shown that the novel design features disclosed herein do in fact allow bristle cluster locations at region of uniformly high activity.

Figure 6:
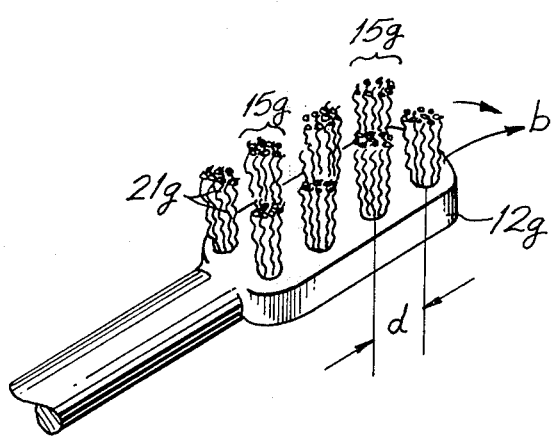
FIG. 6 is a diagrammatic view of applicator means in which the bristles are curled.

In order to understand better the relation between frequency of operation of the disclosed home oral device and the various dimensions of the bristle cluster arrangement and the total toothbrush head herein described for rigid detachable fastening to the ultrasonic motor, we will take a few examples. Let us consider operation first at 30KHz. With a polycarbonate (Lexan) thermoplastic head, we have the wave length, $\tau$, equals 1.86 inches, and so a quarter wavelength corresponds to 0.46 inches. Now, as has been taught herein through FIG. 5 and Table I, the presence of the metal staple elements, together with the bristle clusters, produces an $\alpha$ value substantially less than one. This means that the spacing of bristle clusters relative to the phase of the standing longitudinal waves in the brush head is substantially reduced to a value determined by the numerical value of $\alpha$. For example, with two bristle clusters, b, as shown in FIG. 6, the $\alpha$-effect is magnified and it is readily possible to reduce the 90° phase shift distance, d, by at least fifty percent, which in our 30 KHz example becomes equal to 0.23 inch, or about a quarter of an inch. The distance, d, may be still further controlled and decreased by varying the cross-section of the thermoplastic toothbrush bases 12g and 12h as shown in FIGS. 6 and 7 respectively.

For a frequency of 40KHz, $\tau$ equals 1.4 inches and a quarter wavelength corresponds to 0.35 inch. In this case, distance, d, between the bristle clusters 15g and 15h as described in relation to FIGS. 6 and 7 would be about 0.18 in or about 3/16 of an inch.

If the base were metal, such as aluminum or stainless steel then at 30KHz, $\tau = 6.67$ inches, $\tau/4 = 1.6$ inch. But when we consider the distance, d, the $\alpha$-effect (not considered in the prior patents) would be reversed, because the acoustic impedance of the metal is so much greater than that of the bristle cluster and its epoxy base. In this case, the holes in the metal are filled with a lighter, lower mechanical impedance element and the distance, d, is substantially $\tau/4$ or greater, or at 30KHz, equal to or greater than 1.6 inch. Now, it is evident that this is greater than the whole length of a brush head normally used for toothbrushing and so the novel art disclosed in the instant invention may not be practiced in the prior art disclosed toothbrushes.

Figure 7:
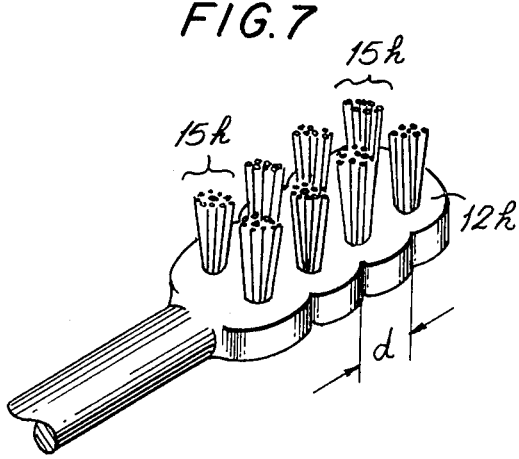
FIG. 7 is a diagrammatic view to help illustrate the present invention.

The correspondence between FIGS. 6 and 7 and the design structure of a toothbrush in the present invention may be clearly seen in FIGS. 10–17, inclusive, FIG. 6 illustrating bristle elements 21g having a curled like configuration.

Figure 8:
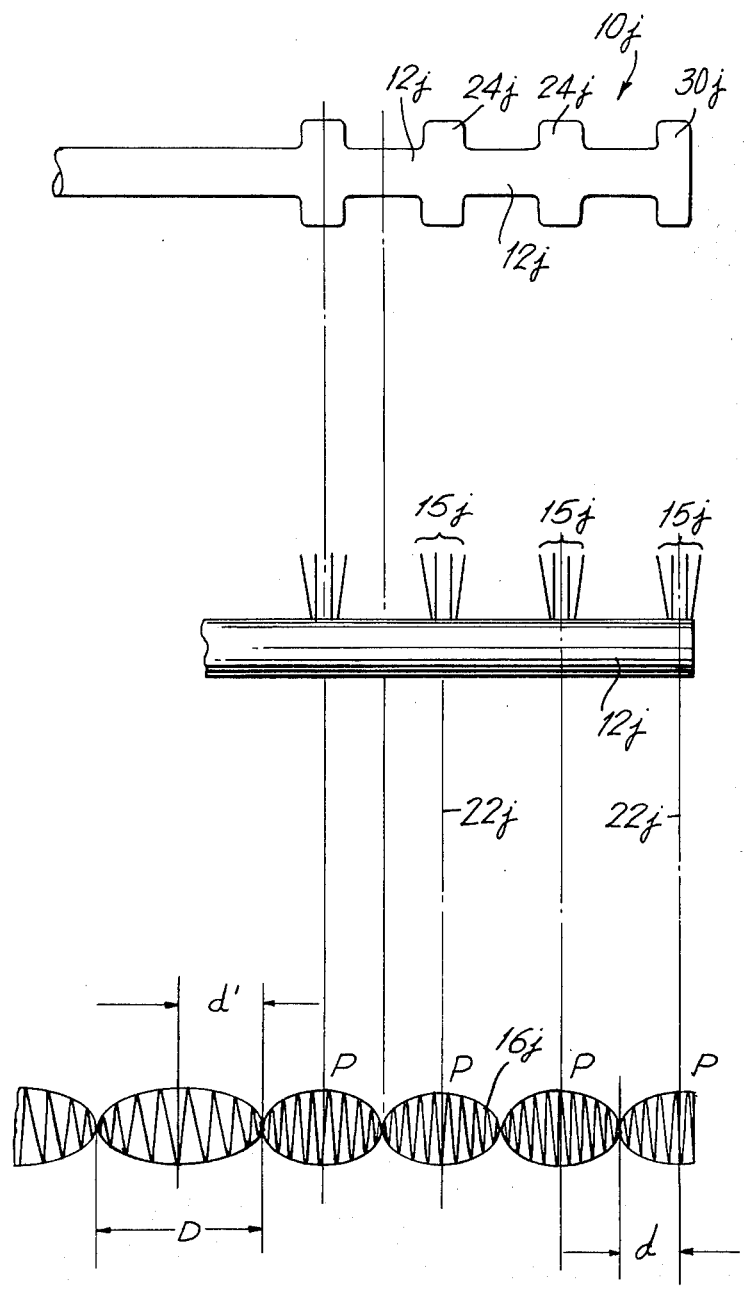
FIG. 8 is a diagrammatic view to help illustrate the theory of the present invention.

As can be seen in FIG. 8, the design has been accomplished whereby the toothbrush 10j has bristle clusters 15j in regions on the base 12j, P, along the verticle plane defined by line 22j are in regions of peak amplitude of vibration as in the curve 16j due to the transmission line effects discussed above. In particular radial sections 24j are in effect the equivalent of the combined mass at the base or the bristle clusters 15j. It will be noted that, in order to conform with the theory, it is desirable to place the bristle clusters 15j at the very end of the toothbrush base 12j so that the portion 30j is shorter in length than the portion, 24j as shown. Also the distance D is equal to a half wavelength in the thermoplastic toothbrush transmission member, needed to screw on the brush to the motor. Accordingly, d' is a quarter wave, which in turn as we have shown is larger than the distance, d, which in its turn depends on the value of $\alpha$ which may be chosen in the various ways disclosed. For Lexan at 30KHz, a half-wave length, D, is about 0.93 inch. Therefore, in making a usable toothbrush according to the teaching of this invention, the size and depth of the mouth (oral cavity) must be at least three inches, and so must incorporate a number of half-wavelengths (180° phase shift) or a number of 90° phase shifts in the node to loop distribution in going from the attachment point to the end of the brush head. A typical Lexan head with nylon bristles operating at about 30KHz would include eleven or twelve 90° phase shift elements in the three-inch length of the disclosed detachable toothbrush. A toothbrush head having a metallic base is designed and is therein taught as a fraction of a 90° phase shift.

Thus, applicants believe they have shown the sophisticated design features of the disclosed invention herein, and have adequately related it to the prior art. To summarize, applicants have found the sophisticated approach herein described with the whole interrelated combination of production and design features to be essential to the creation of an ultrasonic toothbrush which can be mass-produced with associated motor-converters within a cost basis making possible for the first time to have an effective toothbrush at consumer prices. This is the essential step to making oral hygiene control in the home possible, with benefits inherent in the ultrasonic approach and which benefits cannot be otherwise created.

PREFERRED EMBODIMENTS

FIG. 9 illustrates the ultrasonic system 40 which includes instrument means 42 in combination with converter means 44 that work in unison to perform a variety of applications as for example that of tooth brushing. The ultrasonic system 40, for example, is designed to permit the daily use by a person in the home of a toothbrush, whose bristles are mechanically vibrated in a dual frequency in that there is introduced a very low level of high frequency mechanical vibration and, the total power level introduced into the bristles being considerably less than 1 watt.

In addition to the functions performed by an ordinary non-electric traditional toothbrush, the ultrasonic system 40 provides a local action, due to the invisible very low speed microscopic excursions of the individual bristles 45. These low speed invisible reciprocal motions, in combination with saliva or saliva assisted with a suitable dentifrice, provide beneficial stimulation of the gingiva, especially at the tooth-gingiva junction regions, as well as a removal of plaque, which is generally recognized as a principal source of calculus formation and possibly subsequent loss of teeth due to periodental disease.

Thus, to recapitulate, the purpose of the ultrasonic system 40 when used with bristle elements is to provide a person with a device to use in the home and thereby assist the dentist in achieving a significant care of the teeth and gums, in order to help prevent the onset of periodental disease.

The instrument means 42 includes handle means 46 adapted to be held by the user in a conventional manner, and also having the detachable applicator means or assembly 10 containing the bristle clusters or stimulants 15 to be ultrasonically vibrated. Extending from one end of the instrument means 40 thereof is supply means 48 which supplies to the instrument means 42, power from the generator or power means 44 which may have an electrical cord 49 connected to a plug 50 adapted to be plugged into a standard electrical outlet; i.e., 60 cycles per second. Switching means 52 of the generator 44 includes a switch 54 for providing power for energizing the ultrasonic transducer or motor contained within the instrument casing or housing means 46 of the hand held instrument means 42. The energy from the generator 44 is transmitted to the ultrasonic motor by wires extending through the flexible conduit 56 of the power supply means 44. There exists a multi-frequency form of vibrations at the bristle clusters 15 and in the high frequency range illustrated by the double headed narrow 60 which forms a synergistic cooperation of a number of special properties inherent in the total system.

The complete assembly for use in the home includes the generating means 44, for example, a transistorized oscillator capable of producing electrical oscillation at a frequency in the ultrasonic range, as defined herein and the sonic range as defined herein. In practice, the generator 44 may be as small from 1 to 4 watts and generally in the range of 1 to 10 watts, and is preferably of the solid state type. It is desired to employ an oscillation generator, which automatically adjusts to the resonant frequency by reason of the changes occurring in the latter as the applicator member 10 is driven and engages the teeth and gums of the human being cleaned. Such changes in the resonant frequency of the mechanically vibrating unit occur by reason of the fact that the natural frequency of the applicator head 10 will vary with the load placed upon it which might be water, saliva, dentifrice, etc.

The electrical assembly 44 automatically activates the ultrasonic motor 45 in the handpiece housing 46, which in turn transmits modulated high frequency ultrasonic vibrations to the bristle clusters 15 at the end of the applicator means in the form of a plastic transmission line connected detachably to the ultrasonic motor input. The modulation of the high frequency vibrations is, for example, a 60 cycle component which is supplied through the electric converter assembly 44 directly to the bristle clusters 15. The low rate of vibration may be in the range of 10 cycles to 1,000 cycles per second.

By way of example for home consumer application in a tooth brush, the power drawn by the electric converter assembly 44 may be in the range of 1 to 10 watts. The power delivered to the ultrasonic reciprocal motor 45 in the handpiece is under two watts. The mechanical power delivered to the bristles and subsequently into the gingiva and teeth of the user is variable depending upon the pressure and movement of the bristles by the hand of the user. But, in any case, this power under maximum conditions is but a minute fraction of the power delivered to the handpiece is consumed in overcoming electrical and mechanical dissipation of the motor reciprocal motion and toothbrush element.

Essentially, the motor construction, as hereinafter described, is designed depending upon the use thereof to accept a variety of applicator means 10 and the magnitude of ultrasonic mechanical vibrations to be imparted thereto may be selected by proper motor design. The motor includes a transmission member which has a rear section within the housing 46 and a front section 62 extending beyond the casing 46.

The ultrasonic motor in conjunction with the applicator means 10 is longitudinally dimensioned so as to have lengths which are generally whole multiples of half-wavelengths of the compressional waves established therein at the frequency of the combines longitudinal length of the components so that longitudinal loops or other components of motion occur at the end of the applicator means 10. Thus, the optimum amplitude of longitudinal vibration and hyperaccelerations of transmission is achieved, and such amplitude is determined by the relationship of the motor and applicator means 10.

Now referring more particularly to FIGS. 10–13, there is illustrated the applicator means 10 which is designed to be used with the ultrasonic instrument means 40 as previously illustrated with respect to FIG. 9. The applicator means 10 includes a base or body section means 12 with a longitudinally spaced apart ends 63 and 64 and having a brush head or head portion 65 which is the upper section in which the bristle clusters 15 are contained and a spaced apart lower portion or end 66 with a middle section or portion 68 extending therebetween. The body portion 12 which is preferably made out of a thermoplastic material such as Lexan has associated therewith securing means 70 at the lower portion 66 in the form of a securing member 72 inserted at one end thereof having a mating portion 74 in the form of threads which is adapted to mate with a complimentary threaded portion 76 of the lower portion 66. To be maintained firmly in place, a bonding material or cement 77 is used to secure and maintain intimate coupling between the threaded portion 74 and the surrounding lower portion 66.

The securing member 72 includes a gripping section 78 which is shown to be of a hexagonal shape so as to be readily grasped between fingers of the user or a wrench for obtaining the disengagement of the applicator means 10 from the oral device. A stud 80 extends from the opposite end of the gripping section 78 and has a thread that may be of a quick type in that it is not a fine thread so that a minimal number of turns of the applicator means 10 is required before the bottom edge 82 abuts the complimentary surface of the instrument means. A sleeve 88 of a plastic material is postioned over the gripping section 78 and the lower portion 66.

The middle section 68 of the body portion 61 may be designed in a manner in which it has an axially extending bore 84 which extends longitudinally therethrough such as to properly balance the mass of the brush to maintain maximum amplitude of vibration at the output end or tips 85 of the respective bristle clusters 15. The bristle clusters 15 are positioned in a plane substantially normal to the longitudinal axis of the body portion 12 but each individual cluster includes a plurality of bristles 21 that are essentially folded over as seen in FIG. 13 and retained in place by retaining means 90 in the form of a staple 92 having spaced apart prong portions 94 with tips 95 and a connecting portion 96.

Accordingly, each bristle cluster 15 is assembled into an aperture 98 generally of a circular cross-sectional area having an opening 100 at the face surface 102 of the head portion 65 and extending axially the distance generally in the range of 0.10 to 0.250 inch in depth such that each bristle element 21 is formed in a U-shaped manner and held in place by the connecting portion 96 of the staple 92 as the prongs 94 are imbedded into the plastic material of the head portions 65. In this manner, by automatic assembly equipment, the birstle clusters 45 are inserted within the respective apertures 98 and initially held in place. The head portion 65 may have a rectangular cross-section as seen in FIG. 11 whereas the middle portion 68 may be or a circular cross-sectional area with a radius 104 blending the two sections together.

Applicants discovered that the mere introduction or retention of the bristle clusters 45 within an aperture 98 was not sufficient to permit a transmitting of the ultrasonic energy to the respective bristle elements or strands 21 so as to affectuate efficient ultrasonic motion at the bristle tips 85. It is for this reason that applicants discovered that transmitting means 105 was required in order to permit proper acoustical transmission of the vibrational energy waves from the head portion 65 to the respective individual bristles 21. To accomplish this, applicants devised a process wherein the bristles 21 were exposed to a chemical solution 106 having the ability to form a bond for transmission of the energy waves.

Accordingly, to obtain the proper transmission of mechanical vibratory energy both in the sonic range generally in the frequency range of 0.01 KHz to 1 KHz and in the ultrasonic range of 5 KHz to 50 KHz, applicants utilize the process of manufacture in which the aperture 98 to receive the bristle clusters 45 are generally approximately 30% larger than those used in standard brush manufacturing procedures to allow for lesser yield of the thermoplastic material which may be a polycarbonate of various types; i.e. sold under the trademarks, Lexan, Merlon or Polycarbafil. The next step of the manufacturing procedure is to elevate the temperature of the thermoplastic material to a temperature which prevents fracturing of the material upon the insertion of the bristle cluster 15 and the staple 92. Applicants have found that for Lexan material, that the Lexan may be just heated as by inserting in boiling water prior to the insertion of the combined staple 92 and bristle cluster 45 with the temperature of the Lexan being at approximately 212° F. Furthermore, applicants have found that it is possible to use the highest possible density; i.e., maximum number of bristles per staple bunch to make the tightest fit for the insertion thereof. In addition, the staple selected is one having a rounded cross-sectional area rather than a cutting type that is used in certain conventional toothbrushes. This is important in that it prevents partial cutting of the bristles and possible subsequent fatiguing at the point of cut and in turn, a fracturing of the bristle thereby reducing its energy transmission properties.

To assure that the energy is transmitted, the coupling agent which may be in the form of a solvent which causes a flow of the aperture wall as seen in FIG. 15 to the interstices as by the formation of a plurality of fingers 106 that secure each bristle 21 for energy coupling. Accordingly, the solvent is used and causes a flow of the thermoplastic material in the aperture 98 around the staple 92 and bristles 21 thereby assuring proper coupling of the vibratory energy. One type solvent used is Methylene Chloride which is applied when the brush head 61 is at an elevated temperature in the range of 100° F. to 250° F. As seen, this flow of the brush head portion 65 causes an interlocking relationship such that essentially major air gaps are eliminated. In this way the mechanical vibratory energy is properly transmitted to the individual bristles 21 from the brush head 65.

A further novel feature of the present invention is that the ends 85 of each bristle 21 as seen in FIG. 16 are "rounded" such that the sharp points and burrs produced by cutting to size are eliminated. The process for eliminating the sharp points can be attained by either abrasive blasting in that an abrasive compound driven by air pressure being directed against the bristle ends 85 occurs, or another approach is a heating of the bristle ends 85 to cause a momentary softening of the bristle ends and the bristle ends 85 tends to flow and produce a ball-type end 86 to avoid the sharp edge. Applicants have found that the use of Nylon material proves to be most satisfactory for the material from which the bristles 21 are made. The bristle diameter may be in the range of 0.004 inch to 0.020 inch and extend from the brush head a length from 0.30 inch to 0.60 inch. For example, for a bristle cluster that includes eighty ends, the bristle element may have a diameter of 0.008 inch and the aperture 98 a diameter of 0.093 inch and a depth of approximately 0.120 inch.

Now referring more particularly to FIGS. 17–20, there is illustrated the applicator means 10j which may be manufactured as by injection moulding and is designed to be used with the ultrasonic instrument means as previously illustrated. The applicator means 10j includes a base or body section means 12j with a longitudinally spaced apart ends 63j and 64j and having a brush head or head 65j portion which is the upper section in which the bristle clusters 15j are contained and a spaced apart lower portion or end 66j with a middle section or portion 68j extending therebetween. The body portion 12j which is preferably made out of a thermoplastic material such as Lexan has associated therewith securing means 70j at the lower portion 66j in the form of a securing member 72j inserted at one end thereof having a mating portion 74j which is adapted to be secured as by moulding in the lower portion 66j. To be maintained firmly in place, an annular recess or depression 108j is provided to maintain intimate coupling between the portion 74j and the surrounding lower portion 66j.

The lower portion 66j includes a gripping section 78j which is shown to be of a shape with indents 110j so as to be readily grasped between fingers of the user for obtaining the disengagement of the applicator means 10j from the oral device. A stud 80j extends from the securing means 70j approximate the gripping section 78j and has a thread that may be of a quick type in that it is not a fine thread so that a minimal number of turns of the applicator means 10j is required before the bottom edge 64j abuts the complimentary surface of the instrument means.

The bristle clusters 15j may be coupled in position as discussed above.

Along the line improved efficiency factors belongs the providing on the brush head 65j with a material which prevents transmission of high frequency vibratory energy into liquids or teeth or gums. This is readily accomplished, for example, with a closed cell rubber guard or insulating means 115j which may be in the form of a cap 116j. The insulating means may be made of a foam polystyrane or closed cell rubber which presents to the vibrating surface an acoustic impendance equivalent to that of an air film. The acoustic impedance of air is so mismatched (i.e., so much smaller) than the acoustic impedance of the brush head 65j that all ultrasonic energy waves arriving at the brush head-closed cell film interface will be almost totally reflected back into the plastic thereby making more energy available to the bristle clusters 15j to do their work. The cap 116j may be moulded in place and cover substantially just the brush head 65j or the complete brush 10j. If desired the cap or cover 116j may be of a snap-fit onto the brush head 65j as shown with spaced apart side walls 117j, end walls 118j end top wall 119j integrally formed with each other.

Turning now to FIGS. 21 and 22 we have illustrated one of the desired objectives of the invention which relates to the individual bristles of each cluster to deliver their ultrasonic vibrational energy to the load (i.e., gingival and tooth surfaces) as effectively as possible. This means, in detail, that we are trying to deliver a number of types of transfers relating to:

1. Cavitation (for pervasive interproximal effects)
2. Micromassage (for stimulation of local tissue microstructures)
3. Other sonochemical and sono - physiological effects (such as desensitizing, anaesthetizing, mouth wash "psychological" action, fluoride penetration, etc.)

It is found that the overall effectiveness of a straight bristle 21k as illustrated in FIG. 21 in certain instances, is less than a crimped bristle 21m of the type illustrated in FIG. 22 for the same basic diameter. The technical reasons for the difference in behavior are difficult to pinpoint because of the complex character of the vibration transfer from the base of the bristle cluster to the individual bristle of the cluster. But essentially the longitudinal motion of the brush head 65k and 65m as indicated by the double headed arrow 61k and 60m is translated into a flexural type motion at the bristle tips as indicated by double headed arrows 111k and 111m.

With respect to cavitation effects, the increase surface area is undoubtedly a cause for increased efficiency. The "curliness" also provides a more universal field of motional vibration components which increases the overall effectiveness of the various actions. Especially in connection with cleaning out alba (the white matter between teeth due to food) and plaque (the gel-like substance produced by slivary bacteria) which are both soft, the crimped or curly cluster of bristles 21m has a "spring-back" action characteristic of springy curls or spiral springs, which is a combination of the stick-slip effect due to the pulses on-off bursts of ultrasonic energy packets and the low frequency action consequent on this effect and referenced elsewhere in this specification.

Thus, although the crimped bristles are not essential to the operation of the disclosed invention, they nevertheless represent a novel feature of the invention itself, being one of the many disclosed items which increases the effectiveness of the tooth hygiene desired.

Turning now to FIGS. 23–26, there is illustrated the applicator means 10 in use in a dental cleaning procedure in accordance with the invention in operative position in the oral cavity 120 against the teeth 122. In accordance with the invention, the brush bristles 21 of the applicator means 10 is positioned against the teeth 122 in the usual manner during the brushing operation. That is, the bristle clusters 15 are inserted in the mouth and positioned adjacent the tooth surfaces 124 with a relatively light pressure. The bristle clusters 15 may be moved manually to pass the brush portion across all of the tooth surfaces, the bristles 21 randomly assume positions in contact with and displaced from tooth surfaces. Since in the case of manual brushing, the bristle tips 85 rarely assume positions such that they extend deeply into the interproximal areas 126 the present brush is designed to approximate the curvature thereof.

In this manner the action between the sonic motion and ultrasonic motion is believed to result in a combination effect such that the beneficial features of each frequency is simultaneously obtained.

Accordingly, the removing of plaque of 128 on the tooth surface 124 and foreign deposits 130 are obtainable with the present invention. In FIG. 23 plaque 128 is illustrated as a layer of material that has adheres to the surfaces of the teeth 122. Plaque is a soft gelatinous substance produced in the mouth by the action of salivary and sub-gingival bacteria, hardens into calculus in a period of from two to twelve days, and is believed to be a significant factor in causing periodental diseases.

In use, the ultrasonic bristles clusters 15 are vibrated so as to introduce a micro-motion and a macro-motion to the teeth surfaces as by generating ultrasonic vibrations as illustrated by the double-headed arrow 60 in the bristle elements 21 at the working end of the hand held ultrasonic motor that is in turn coupled to the brush head 65. By amplitude modulating the ultrasonic vibrations at a sonic rate there is produced alternating periods of ultrasonic vibrating activities at the bristle elements and periods of rest or substantially zero ultrasonic vibrations. Then by engaging the bristle tips 85 against the teeth surface 124 and maintaining a relative moving relationship there is generated sufficient action to remove the plaque 128 and interproximal deposits 130.

This action is generally obtained by providing a fluid film as illustrated by the particles 132 which may be in the form of a dentifrice having certain characteristics or simply that of saliva. The motion at the bristle tips 85 is of sufficient amplitude of vibrations to also produce a cavitational action in the fluid film 132 by the bristle elements 21.

Accordingly, FIGS. 23–26 inclusive are diagrammatic views helpful in explaining how the interrelated phenomena are believed to simultaneously occur to obtain the improved cleaning results. The user applies the applicator means 10 in a manner so as it is longitudinally vibrated in the direction of two-headed arrow 60 with respect to microscopic action. Mechanical vibratory energy is transmitted to the free ends 85 of bristle clusters 15 and through a fluid or other medium 132, or directly by contact with teeth surface 124.

In use then, the applicator means 10 is inserted in the oral cavity of the user and may be maintained in fixed position relative to a number of teeth as, for example, illustrated in FIG. 23 such that the cavitational and other actions may occur as the bristle clusters 15 are maintained in relatively light contact with the teeth surface 124 as well as the gingival surfaces of the mouth. If the user desired, he may move the applicator means 10 across the surface of the teeth as well as the gingival surfaces to obtain the desired results. When movement occurs, the bristle clusters will assume various positions and, for example as seen in FIG. 26, two bristle clusters 15 are in contact with a single tooth 122 so that the plaque material 128 may be microscopically removed therefrom. The ultrasonic energy introduces the micro-motion in the bristle clusters 15 which is responsible for certain cavitational effects that will be engendered between various clusters 15 depending upon the particular fluids 132 in use and the make-up thereof.

Accordingly, the inducement of the vibrations in the bristle elements are at an ultrasonic range of 10KHz to 500KHz to vibrate the bristle elements longitudinally and the vibration of the bristle elements at a low sonic frequency at the range of 0.01 KHz to 1 KHz produces the cleaning. As the brushing occurs there is maintained an amplitude of vibrations at the bristle elements 21 sufficient to obtain a cavitational action on the teeth surfaces 124.

The bristle elements 21 as seen particularly in FIG. 26 may have a contoured surface configuration that lend themselves to conform to the contour of teeth 122 such that the bristle elements form a surface consisting of a multiple number of pointed members interproximately to the teeth during the brushing thereof which produces peak accelerations in the bristle elements.

One aspect of the present invention is to provide insulating means 115 that may surround the toothbrush head 65 to improve efficiency in that the insulating means 115 may be of a material which prevents transmission of high frequency vibratory energy into liquid or teeth or gums.

This is readily accomplished, for example, with a closed cell rubber sheet. The closed cell material presents to the vibrating surface an acoustic impedance equivalent to that of an air film. The acoustic impedance of air is so mismatched (i.e., so much smaller) than the acoustic impedance of the brush head plastic 65 that all ultrasonic energy waves arriving at the brush head-closed cell firm interface will be almost totally reflected back into the plastic thereby making more energy available to the bristle clusters 15 to do their work.

For example, a very mild abrasive dentifrice could be used or, if desired, saliva or regular water may be used depending upon the contition of the user's mouth at the time he starts using the present invention. The macro-motion provided by the low sonic frequency energy in a sense permits a flushing away aspect in that gross motion is simultaneously obtained with respect to the interaction between the various frequencies and thereby helps in the manual brushing concept. The low sonic rate also helps the user phychologically in knowing that the instrument is working, since the ultrasonic aspect is above the audible range of the user. Furthermore, a micro-massage of the guns of the user is also obtained. The utilization of the applicator means 10 is such that it may be positioned against the various surfaces of the teeth as illustrated in FIGS. 24, 25, and 26 as would normally be the case with the positioning of a conventional cleaning operation.

The ultrasonic energy available at the bristle tips provide a number of beneficial results, which result in the plaque and other foreign deposits to be removed from the teeth. Accordingly, the brush of the present invention permits stimulation of the gingival tissue by macro-massage and micro-massage which has been found beneficial for dental health, and massage also results in more blood circulation than is obtained by conventional brushing techniques.

The angular positionment of the bristle clusters 15 with respect to the applicator means 10 are substantially normal to the longitudinal mode of vibration, but these may be varied, as well as the fact that an oscillatory or radial mode of macro-motion may also be applied to the applicator means 10 other than pure longitudinal motion. Furthermore, the length and stiffness of the various bristles may be varied within the confines of the present invention and the beneficial results may still be obtained.

Figure 27:
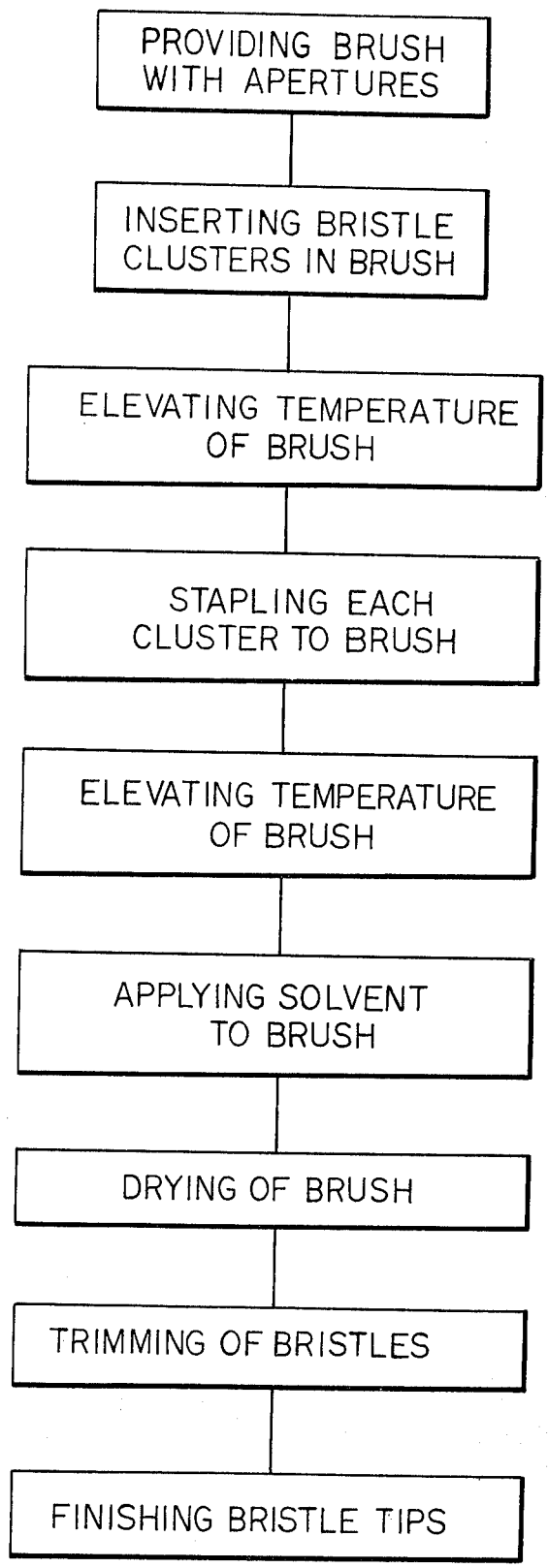
FIG. 27 is a block diagram illustrating the method of manufacturing the brush of the present invention.

Referring now to FIG. 27, applications herein disclose the method of manufacture of the brush previously described and ideally suited for use with an instrument that drives it at an ultrasonic as well as sonic rate. Initially, the ultrasonic applicator or brush 10 is formed either by machining or injection molding such that the brush head portion has a plurality of the spaced apart apertures 98 contained therein and adapted to receive a plurality of individual bristles therein.

By conventional equipment well known in the art, the step of inserting and stapling the respective bristle clusters 15 in each respective aperture 98 is accomplished and may be carried on in an automatic process. It has been found that, if the stapling operation occurs when the brush head is at room temperature, that a certain degree of cracking or crazing will occur as the staple is driven into the brush head or more particularly when the brush is ultrasonically vibrated. Accordingly, the brush head by heating is elevated to a temperature in the range of 100° F to 250° F, and for Lexan about 212° F prior to stapling each bristle cluster 15 in place. The staple is of a conventional form and, for example, may be of 0.024 inch diameter made of 302 stainless steel, ¼ hard.

After this is accomplished, the temperature of the brush head for a brush made of Lexan material is raised to and stabilized at approximately 135° F, and the entire brush or the brush head alone, is dipped in a liquid solvent such as methylene chloride, such that the applying of the solvent covers the entire brush and particularly seeps into the points between the aperture wall and the outer surface of the respective bristles of the cluster. After this occurs, the excess solvent may be removed by an air jet or other means. The next step in the operation is the drying of the brush such that the solvent is removed and this may occur by returning the brush to the oven which may be at a temperature of approximately 150° F and retaining the brush in the oven at that temperature for approximately one half hour. As a result of the above steps, there occurs a flow of the plastic in the brush head portion into surrounding relationship of the bristles in each aperture therein such that the plastic solidified in adhesive relationship to the bristles to transmit the ultrasonic vibratory energy from the brush head portion to the bristles. The fluidized plastic produces intermittent molecular contact to fill the interstices and provide an adhesion for acoustical transmission of energy. Accordingly, the brush of the present invention is manufactured and proper transmission of the vibratory energy is obtained as previously explained.

Generally subsequent to the above, the next step is that of trimming or cutting of the bristle clusters to a desired shape as by shearing thereof such that the vibratory tips of the bristles may have the configuration desired.

The next step in the manufacture is the finishing of the bristle tips 85 to a desired shape or contour and this may occur as by sort of a polishing or sand blasting process or, if desired, the tips 85 of the respective bristle elements 21 may be exposed to a heat source so, as seen in FIG. 16, a rounded edge occurs.

If the brush is designed in that the securing means are coupled to the brush as by threads, then prior to elevating the temperature of the brush for stapling, the solvent or wetting agent may be applied to the threaded portion 74 of the securing member 72 as well as to the thread 76 of the brush and then the parts may be screwed together tightly and the temperature of the entire brush elevated as discussed above prior to dipping of the entire brush in the solvent.

In addition, the step of applying the sleeving 88 to the brush is accomplsihed by using a shrink-type tubing that is axially slipped over the body and the securing means 70. Subsequent thereto, the temperature of the sleeving may be increased as by applying heat thereto and shrinking the tubing in place.

To acoustically insulate the head portion 65 of the brush 10 from its transmission of vibratory energy to the cheek of the user, an insulating material may be secured to the head portion as by an adhesive or other means.

CONCLUSION

Accordingly, the toothbrush hereinabove illustrated is one embodiment that may be employed with a power handle so as to properly deliver the ultrasonic vibrational energy to the bristle tips and be suitable for production on a mass basis. It will be appreciated by those skilled in the art that various modifications and devices may occur to the disclosure of the present invention, but the same are generally illustrated as being secured to the power source by securing means that may vary in shape or size and that the means may even be an integral part of the brush itself and be molded therewith to eliminate the necessity of another component part to be added to the brush.

While certain novel features of this invention have been disclosed herein and are pointed out in the claims, it will be understood that various ommissions, substitutions, and changes may be made by those skilled in the art, without departing from the teachings of the invention.

We claim:

1. The method of manufacturing toothbrush adapted to be mounted on an automatic toothbrush power handle having as a power source vibratory energy in the ultrasonic range, comprising the steps of:
   A. providing a plastic brush having a head portion including a plurality of apertures therein;
   B. positioning of bristle cluster respectively in each aperture;
   C. changing the shape of the aperture by effecting a flow of the plastic in said respective aperture into substantially surrounding relationship with the bristles in each aperture therein, whereby the plastic solidifies in adhesive relationship to the bristles to transmit the ultrasonic vibratory energy from the brush head portion to the bristles; and
   D. coupling to said brush securing means adapted to be coupled to said power handle.

2. A method as defined in claim 1, and further including the step of stapling each bristle cluster within its respective aperture.

3. A method as defined in claim 2, and further including the step of heating said head portion prior to inserting a staple therein.

4. A method as defined in claim 3, wherein said head portion is elevated in temperature in the range of 100° F. to 250° F.

5. A method as defined in claim 1, wherein said step of effecting a flow of the plastic in said head portion further includes the steps of
   a. elevating the temperature of said head portion,
   b. applying a solvent to said head portion in the vicinity of said apertures, and
   c. drying said head portion.

6. A method as defined in claim 5, wherein said brush head is of polycarbonate material.

7. A method as defined in claim 5, wherein said solvent is methylene chloride.

8. A method as defined in calim 5, wherein said solvent is applied by immersing said head portion and bristles within said solvent.

9. A method as defined in claim 8, and further including the step of removing any excess solvent from said head portion.

10. A method as defined in claim 1, and further including the step of rounding the bristle ends.

11. A method as defined in claim 10, wherein said rounding is obtained by an abrasive material.

12. A method as defined in claim 10, wherein said rounding is obtained by heating the individual bristles of said bristle cluster.

13. A method as defined in claim 1, and further including the step of applying a sleeving in axial relation to said securing means.

14. A method as defined in claim 1, wherein said bristles are crimped.

15. A method as defined in claim 1, and further including the step of cutting the bristles to a defined length.

16. A method as defined in claim 1, and further including the step of drying said brush after effecting said flow of the plastic.

17. A method as defined in claim 1, wherein said bristles are of polycarbonate.

18. The method of manufacturing a toothbrush adapted to be mounted on an automatic toothbrush power handle having as a power source vibratory energy in the ultrasonic range, comprising the steps of:
   A. providing a plastic brush with an integrally formed brush head portion having a plurality of apertures therein,
   B. positioning a bristle cluster respectively in each aperture,
   C. simultaneously inserting a staple in each cluster to the brush head,
   D. elevating the temperature of said brush head,
   E. applying a solvent to said brush head while said brush head is in its elevated temperature, whereby said solvent effects a flow of the plastic material adjacent each bristle cluster within its respective aperture such that the plastic flows and thereafter solidifies in adhesive relationship to the bristles to transmit the ultrasonic vibratory energy from the brush head to the respective bristles,
   F. drying the solvent off of said brush head,
   G. trimming said bristles to a desired length, and
   H. finishing the respective bristle ends.

19. A method as defined in claim 18, wherein said solvent is applied by immersing said brush head and bristles within said solvent.

20. A method as defined in claim 19, and further including the step of removing any excess solvent from said brush head.

21. A method as defined in claim 18, and further including the step of coupling to said brush securing means adapted to be coupled to said power handle.

22. A method as defined in claim 18, and further including the step of applying to said brush head vibration absorbent material.

23. A method as defined in claim 18, and further incuding the step of cutting the bristles to a defined length.

24. A method as defined in claim 18, wherein said bristle ends are rounded.

25. The method of manufacturing a toothbrush adapted to be mounted on an automatic toothbrush power handle having as a power source vibratory energy in the ultrasonic range, comprising the steps of:
A. providing a plastic brush having a head portion including a plurality of apertures therein;
B. positioning a bristle cluster respectively in each aperture;
C. changing the shape of the aperture by effecting a flow of the plastic in said respective aperture into substantially surrounding relationship with the bristles in each aperture therein, whereby the plastic solidifies in adhesive relationship to the bristles to transmit the ultrasonic vibratory energy from the brush head portion to the bristles; and
D. applying to said head portion vibration absorbent material.

* * * * *